US006384189B1

(12) United States Patent
Murphy-Ullrich et al.

(10) Patent No.: US 6,384,189 B1
(45) Date of Patent: May 7, 2002

(54) COMPOSITIONS FOR STIMULATING TGF-β ACTIVITY

(76) Inventors: Joanne E. Murphy-Ullrich, 939 Landale Rd., Birmingham, AL (US) 35222; Stacey Schultz-Cherry, 1501 Valley View Dr., Birmingham, AL (US) 35209; David D. Roberts, 6808 Persimmon Tree Rd.; Henry C. Krutzsch, 9704 DePaul Dr., both of Bethesda, MD (US) 20817

( * ) Notice: Subject to any disclaimer, the term of this patent is extended or adjusted under 35 U.S.C. 154(b) by 0 days.

(21) Appl. No.: 08/871,561

(22) Filed: Jun. 10, 1997

Related U.S. Application Data

(63) Continuation of application No. 08/238,169, filed on May 4, 1994, now abandoned, which is a continuation-in-part of application No. 08/106,120, filed on Aug. 13, 1993, now abandoned.

(51) Int. Cl.$^7$ ............... C07K 9/00; C07K 7/00; C07K 5/10; C07K 5/08

(52) U.S. Cl. ............ 530/326; 530/328; 530/329; 530/330; 530/331; 530/402; 530/403

(58) Field of Search ............... 530/300, 324, 530/325, 329, 330, 350, 326, 327, 331, 402, 403

(56) References Cited

U.S. PATENT DOCUMENTS

| | | | |
|---|---|---|---|
| 5,028,425 A | * | 7/1991 | Good et al. |
| 5,190,918 A | | 3/1993 | Deutch .............. 514/15 |
| 5,192,744 A | | 3/1993 | Bouck ............... 514/8 |
| 5,312,899 A | * | 5/1994 | Schiller |
| 5,674,503 A | * | 10/1997 | Olafson et al. |
| 5,770,563 A | * | 6/1998 | Roberts et al. |
| 5,824,647 A | * | 10/1998 | Postlethwaite et al. |
| 5,840,691 A | * | 11/1998 | Furcht et al. |

FOREIGN PATENT DOCUMENTS

| | | |
|---|---|---|
| EP | 0 350 221 A | 1/1990 |
| WO | WO93 11156 A | 6/1993 |
| WO | WO95 28832 A | 11/1995 |

OTHER PUBLICATIONS

Suzuki et al. Chem Abstracts 65: col. 17043, 1966 (Abstract.*

Ishii Chem Abstracts 56:5054b 1962.*

Catalog: "s13" *Bachem Feinchemikalien AG*, pp. 59–60, 188, 351, 499, 500, 502–503, 528–529, 1993.

Frazier, William A. "Active Peptide Sequences in the Cell Binding Domain of Thrombospondins" *Methods* 5(3):212–219, 1993.

Schultz–Cherry et al. Abstract RZ225 "Activation of Latent TGF–β by Thrombospondin" *J. Cellular Biochem.* Suppl., 17E, p 164, 1993.

Schultz–Cherry, Stacey and Murphy–Ullrich, Joanne "Thrombosponding Causes Activation of Latent Transforming Growth Factor–β Secreted by Endothelial Cells by a Novel Mechanism" *J. Cellular Biology* 122(4):924, Aug. 1993.

Murphy–Ullrich, Joanne and Schultz–Cherry, Stacey Abstract A315 "Thrombospondin Activates Latent TFG–β Secreted by Endothelial Cells" *J. Cellular Biochem.*, Suppl. 17E, p. 128, Mar. 29–Apr. 25, 1993.

McCaffrey et al. "Transforming Growth Factor–β1 is a Heparin–binding Protein: Identification of Putative Heparin–Binding Regions . . . " *J. Cellular Physiol.* 152:430–440, 1992.

Klar et al. "F–Spondin: A Gene Expressed at High Levels in the Floor Plate Encodes a Secreted Protein that Promotes . . . " *Cell* 69:95–110, Apr. 3, 1992.

Martin–Zanca et al. "Molecular and Biochemical Characterization of the Human trk Proto–Oncogene" *Mol. and Cellular Biol.* 9(1):24–33, Jan. 1989.

Lahav, Judith, "The Functions of Thrombospondin and its Involvement in Physiology and Pathophysiology," *Biochimica et Biophysica Acta,* 1182:1–14 (1993).

Rifkin, Daniel B. et al., "TGF–β: Structure, Function, and Formation," *Thrombosis and Haemostasis,* 70(1):177–179 (1993).

Vogel, Tikva et al., "Modulation of Endothelial Cell Proliferation, Adhesion, and Motility by Recombinanat Heparin–Binding Domain and Synthetic Peptides From the Type I Repeats of Thrombospondin," *Journal of Cellular Biochemistry,* 53:1–11 (1993).

Schultz–Cherry, Stacey et al., "Thrombospondin Causes Activation of Latent Transforming Growth Factor–β Secreted by Endothelial Cells by a Novel Mechanism," *The Journal of Cell Biology,* 122(4):923–932 (Aug. 1993).

(List continued on next page.)

*Primary Examiner*—Phillip Gambel

(57) ABSTRACT

The invention provides a method of stimulating TGF-β activity, comprising contacting latent TGF-β with an amount of an activating peptide from TSP effective to convert latent TGF-β to active TGF-β. Also provided is a method of inhibiting the stimulation of TGF-β activity, comprising contacting latent TGF-β with an amount of an inhibiting peptide from TSP effective to inhibit conversion of latent of TGF-β to active TGF-β. The invention also provides a method of enhancing wound healing, comprising the step of administering to the wound site an amount of an activating peptide from TSP effective to convert latent TGF-β to active TGF-β, the activation of TGF-β resulting in enhanced wound healing. A method of preventing excessive fibrosis stimulated by TGF-β in pathology is also provided, comprising administering to a site of potential fibrosis an amount of inhibiting peptide from TSP effective to inhibit conversion of latent TGF-β to active TGF-β, resulting in reduced fibrosis. The invention also provides a method of blocking TGF-β-mediated inhibition of endothelial cell proliferation comprising contacting the endothelial cells with an inhibiting peptide effective to inhibit conversion of latent TGF-β to active TGF-β, resulting in proliferation of endothelial cells.

18 Claims, No Drawings

OTHER PUBLICATIONS

Harris, William J. et al., "Therapeutic Antibodies—The Coming of Age," *TIB Tech,* 11:42–44 (Feb. 1993).

Cromack, Douglas T. et al., "Acceleration of Tissue Repair by Transforming Growth Factor $\beta_1$: Identification of In Vivo Mechanism of Action with Radiotherapy–Induced Specific Healing Deficits," *Surgery,* 113(1):36–42 (Jan. 1993).

Massagué, J. et al., "Transforming Growth Factor–$\beta$," *Cancer Surveys,* 12:81–103 (1992).

Michael B. Sporn et al., "Transforming Growth Factor–$\beta$: Recent Progress and New Challenges," *The Journal of Cell Biology,* 119(5):1017–1021 (Dec. 1992).

Bornstein, Paul, "Thrombospondins: Structure and Regulation of Expression," *The FASEB Journal,* 6:3290–3299 (Nov. 1992).

Border, Wayne A., "Transforming Growth Factor–$\beta$ in Disease: The Dark Side of Tissue Repair," *Perspectives,* 90:1–7 (Jul. 1992).

Murphy–Ullrich, Joanne E. et al., "Transforming Growth Factor–$\beta$ Complexes With Thrombospondin," *Molecular Biology of the Cell,* 2:181–188 (Feb. 1992).

Tuszynski, George P. et al., "Biological Activities of Peptides and Peptide Analogues Derived from Common Sequences Present in Thrombospondin, Properdin, and Malarial Proteins," *The Journal of Cell Biology,* 116(1):209–217 (Jan. 1992).

Dardik, R. et al., "Cell–Binding Domain of Endothelial Cell Thrombospondin: Localization to the 70–kDa Core Fragment and Determination of Binding Chracteristics," *Biochemistry,* 30:9378–9386 (1991).

Osband, Michael E. et al., "Problems in the Investigational Study and Clinical Use of Cancer Immunotherapy," *Immunology Today,* 11(6)193–195 (1990).

Good, Deborah J. et al., "A Tumor Suppressor–Dependent Inhibitor of Angiogenesis is Immunologically and Functionally Indistinguishable from a Fragment of Thrombospondin," *Proc. Natl. Acad. Sci. USA,* 87:6624–6628 (Sep. 1990).

Taraboletti, Giulia et al., "Platelet Thrombospondin Modulates Endothelial Cell Adhesion, Motility, and Growth: A Potential Angiogenesis Regulatory Factor," *The Journal of Cell Biology,* 111:765–772 (Aug. 1990).

Wahl, Sharon M. et al., "Inflammatory and Immunomodulatory Roles of TGF–$\beta$," *Immunology Today,* 10(8):258–261 (1989).

Foon, Kenneth A. et al., "Biological Response Modifiers: The New Immunotherapy," *Cancer Research,* 49:1621–1639 (Apr. 1, 1989).

Mustoe, Thomas A. et al., "Accelerated Healing of Incisional Wounds in Rats Induced by Transforming Growth Factor–$\beta$," *Science,* 237:1333–1336 (Sep. 11, 1987).

Sporn, Michael B. et al., "Polypeptide Transforming Growth Factors Isolated from Bovine Sources and Used for Wound Healing In Vivo," *Science,* 219:1329–1331 (Mar. 18, 1983).

Schultz–Cherry et al. *J. Biol. Chem.* 270:7304–7310, 1995.

Steed et al. *Diabetes Carre* 18:39–46, 1995.

Hansbrough et al. *J. Burn Care Rehabil.* 16:377–387, 1995.

Twedev et al. *J. Heart Valve D.S.* 4 Suppl 1 :590–7 1995 Abstract only.

Shah et al. *J. Cell Science* 107:1137–1157, 1994.

Weathers et al. *Blood* 84:1775–1779, 1994 Abstract only.

Giri et al. *Thorax* 48:959–966, 1993.

Catalog:"s13" Bachem Feinchemikalien AG XP002027514, p. 350, compound nr. H–4210, 1993.

Mohri et al. "Synthetic Peptides Inhibit the Interaction of von Willebrand Factor–Platelet Membrane Glycoproteins" *PeptidesI 14:125–129,* 1993.

Sipes et al. "Inhibition of Fibronectin Binding and Fibronectin–mediated Cell Adhesion . . . " *J. Cell Biol.* 12192):469–477, 1993.

Babizhayen et al. *Mechanisms of Ageing Develop.* 72:1–12, 1993.

Tolsma et al. *J. Cell Biol.* 122(2):497–511, Jul. 1993.

Grant et al. *J. Cell Physiol.* 153:614–625, 1991.

Sakamoto et al. *Blood* 51:903–905, 1991.

Humphries et al. *Science* 233:467–470 (1986).

Khalil et al. *J. Exp. Med.* 170:737–747 (1989).

\* cited by examiner

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Cys Ser Val Thr Cys Gly
1               5

(2) INFORMATION FOR SEQ ID NO:2:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

Trp Ser Xaa Trp
1

(2) INFORMATION FOR SEQ ID NO:3:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Gly Gly Trp Ser His Trp
1               5

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Trp Ser His Trp
1

(2) INFORMATION FOR SEQ ID NO:5:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

Lys Arg Phe Lys
1

(2) INFORMATION FOR SEQ ID NO:6:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

His Arg Phe Lys
1

(2) INFORMATION FOR SEQ ID NO:7:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:7:

Arg Lys Pro Lys
1

(2) INFORMATION FOR SEQ ID NO:8:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

Gln Arg Phe Lys
1

(2) INFORMATION FOR SEQ ID NO:9:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

Lys Arg Phe Lys Gln Asp Gly Gly
1               5

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:10:

Arg Trp Arg Pro Trp Thr Ala Trp Ser Glu
1               5                   10

(2) INFORMATION FOR SEQ ID NO:11:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:11:

Thr Ala Tyr Arg Trp Arg Leu Ser His Arg Pro Lys Thr Gly Ile Arg
1               5                   10                  15
Val (2) INFORMATION FOR SEQ ID NO:12:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:12:

Lys Arg Phe Lys Gln Asp Gly Gly Ala Ser His Ala Ser Pro Ala Ser
1               5                   10                  15
Ser (2) INFORMATION FOR SEQ ID NO:13:

(i) SEQUENCE CHARACTERISTICS:

```
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:13:

Lys Arg Phe Lys Gln Asp Gly Gly Ala Ser His Ala Ser Pro
1               5                  10

(2) INFORMATION FOR SEQ ID NO:14:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

Lys Arg Phe Lys Gln Asp Gly Gly Trp Ser His Trp Ser Pro
1               5                  10

(2) INFORMATION FOR SEQ ID NO:15:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

Lys Arg Phe Lys Gln Asp Gly Gly Trp Ser His Trp Ser Pro Trp Ser
1               5                  10                 15
Ser (2) INFORMATION FOR SEQ ID NO:16:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:16:

Lys Arg Phe Lys Gln Asp Gly Gly Trp Ser His Trp
1               5                  10
```

```
(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:17:

Lys Arg Phe Lys Gln Asp Gly Gly Trp Trp Ser Pro
1               5                   10

(2) INFORMATION FOR SEQ ID NO:18:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:18:

Arg Phe Lys
1

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

Trp Asn Asp Trp Ile
1               5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:20:

Trp Ser Ser Trp Ser
1               5
```

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

Leu Ser Lys Leu
1

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:22:

Ala Ala Trp Ser His Trp
1               5

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

Asp Gly Trp Ser Pro Trp
1               5

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

Gly Gly Trp Gly Pro Trp
1               5

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:25:

Trp Ser Pro Trp Ser
1           5

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:26:

Gly Trp Ser His Trp
1           5

(2) INFORMATION FOR SEQ ID NO:27:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:27:

Trp Ser His Trp Ser
1           5

(2) INFORMATION FOR SEQ ID NO:28:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:28:

Trp His Ser Trp Ala Ala 1               5

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:29:

Val Thr Cys Gly Gly Gly Val Gln Lys Arg Ser Arg Leu
1               5                   10

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:30:

Thr Arg Ile Arg
1

(2) INFORMATION FOR SEQ ID NO:31:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:31:

Ala Arg Phe Lys
1

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:32:

Lys Lys Phe Lys
1

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:33:

Lys Gln Phe Lys
1

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:34:

Lys Arg Phe Gln
1

(2) INFORMATION FOR SEQ ID NO:35:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:35:

Lys Arg Ala Lys
1

(2) INFORMATION FOR SEQ ID NO:36:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:36:

```
Lys Arg Tyr Lys
1

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:37:

Lys Arg Trp Lys
1

(2) INFORMATION FOR SEQ ID NO:38:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:38:

Ala Ser Leu Arg Gln Met Lys Lys Thr Arg Gly Thr Leu Leu Ala Leu
1               5                  10                  15

Glu Arg Lys Asp His Ser
            20

(2) INFORMATION FOR SEQ ID NO:39:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:39:

Glu Leu Thr Gly Ala Ala Arg Lys Gly Ser Gly Arg Arg Leu Val Lys
1               5                  10                  15

Gly Pro Asp (2) INFORMATION FOR SEQ ID NO:40:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide
```

(iii) HYPOTHETICAL: NO (iv) ANTI-SENSE: NO (xi) SEQUENCE DESCRIPTION: SEQ ID NO:40:

Ser His Trp Trp Ser Ser
1               5

(2) INFORMATION FOR SEQ ID NO:41:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:41:

Gly Gly Trp Ser His Tyr
1               5

(2) INFORMATION FOR SEQ ID NO:42:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:42:

Gly Gly Trp Ser Lys Trp
1               5

(2) INFORMATION FOR SEQ ID NO:43:

(i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:43:

Arg Phe Arg
1

(2) INFORMATION FOR SEQ ID NO:44:

(i) SEQUENCE CHARACTERISTICS:
            (A) LENGTH: 3 amino acids
            (B) TYPE: amino acid
            (C) STRANDEDNESS: single
            (D) TOPOLOGY: linear -continued

```
        (ii) MOLECULE TYPE: peptide (iii) HYPOTHETICAL: NO (iv) ANTI-SENSE: NO (xi) SEQUENCE DESCRIPTION: SEQ ID NO:44:

Arg Trp Arg
1

(2) INFORMATION FOR SEQ ID NO:45:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:45:

Lys Arg Phe Lys Gln Asp Gly Gly Trp Ser His Trp Ser Pro Trp Ser
1               5                  10                 15

Ser Cys (2) INFORMATION FOR SEQ ID NO:46:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:46:

Gly Gly Trp Ser His Trp Ser Pro Trp Ser Ser Cys
1               5                  10
```

COMPOSITIONS FOR STIMULATING TGF-β ACTIVITY

This application is a continuation of Ser. No. 08/238,169, filed on May 4, 1994, now abandoned which is a continuation-in-part of Ser. No. 08/106,120 filed Aug. 13, 1993, which status is abandoned.

BACKGROUND OF THE INVENTION

1. Field of the Invention

The present invention relates to a method of regulating TGF-β activity. In particular, the present invention relates to a method of stimulating or inhibiting TGF-β activity by the application of specific peptides.

2. Background Art

Transforming growth factor-β (TGF-β) is a member of a family of growth, differentiation, and morphogenesis autocrine and paracrine factors (3,26). TGF-β can affect diverse cellular functions in virtually all cell types. Depending on the cell type and its extracellular environment, these effects can be either positive or negative. TGF-β inhibits the proliferation of endothelial cells in vitro (31), but stimulates angiogenesis in vivo (39). TGF-β has also been shown to enhance or inhibit the proliferation of fibroblasts depending on the nature of the substrate and the mitogens present (3). Myoblast differentiation can also be induced or blocked by TGF-β depending on the availability of mitogens (25, 45).

TGF-β1 is a disulfide-linked homodimer that is synthesized as part of a latent precursor molecule (26). The latent precursor molecule is 390 amino acids in length and consists of an N-terminal 278 amino acid latency associated peptide (LAP) and a C-terminal 112 amino acid active domain (15–17). The proregion of TGF-β is unique in that it remains non-covalently attached to the active region after intracellular proteolytic processing and secretion (15). Association of the LAP with the mature peptide region confers latency: the LAP-associated growth factor is unable to interact with its cellular receptors. The LAP contains three N-linked glycosylation sites, two of which have mannose-6-phosphate residues (8,28,38). These carbohydrate structures may be important for latency since endoglycosidase F treatment leads to activation of TGF-β (28). The disulfide-bonded dimeric structure of LAP is critical for latency, since site-directed mutagenesis of critical cysteine residues (cys 223, 225) in the LAP abolishes the latency function (9). The active domain contains nine conserved cysteine residues that participate in inter-and intrachain disulfide bonding (27).

TGF-β is secreted by most cell types as a latent complex (27,37). Since TGF-β synthesis and TGF-β receptor expression are not highly regulated, primary regulation of TGF-β activity occurs by controlling conversion of the latent TGF-β complex to the active molecule. Physiochemical activation can occur by extremes of pH, heat, chaotropic agents, and deglycosylation (6,27,28,37). Activation in vivo is more complex and not well understood. There is evidence from cell culture models that activation may occur through binding of the latent molecule to mannose 6-phosphate receptors (12,21), by plasmin-mediated proteolytic processing (4,23,40,41), and/or by processing in acidic cellular microenvironments (20). In some systems, activation of latent TGF-β by plasmin is relatively inefficient (41). In addition, there are reports of TGF-β activation occurring independently of these mechanisms (19). These results suggest that additional mechanisms of latent TGF-β activation may exist.

TGF-β has been demonstrated, through numerous studies, to play a significant role in wound healing and fibrosis. The three phases of inflammation, granulation tissue formation and biosynthesis of the extracellular matrix, are identical in both the wound healing process and the development of fibrosis. A fine balance in the biosynthetic and degradative pathways involved in extracellular matrix biosynthesis appears to be determinative of whether proper wound healing or fibrosis results. Due to its function of regulating genes critically involved in extracellular matrix formation, TGF-β significantly influences this phase of tissue regeneration, the final outcome of which is either wound healing or fibrosis. (46). Thus, sensitive regulation of TGF-β activity in this process will permit control of the wound healing and fibrotic processes.

The thrombospondins (TSP) are a growing family of multidomain glycoproteins (47,48,5,49). TSP1 is the best characterized and serves as the prototypical TSP molecule. TSP is secreted and incorporated into the extracellular matrix of a number of cells in culture (1–5). TSP, like TGF-β, has diverse effects on cellular functions that vary with cell type. TSP can inhibit endothelial proliferation and migration (2,42,34,51), but stimulates the growth of smooth muscle cells and dermal fibroblasts (52,36). TSP may also serve as both an attachment protein and an anti-adhesive molecule as shown by its ability to cause disassembly of focal adhesions in endothelial cells (33). TSP also plays a role in angiogenesis, fibrinolysis, platelet aggregation, and inflammation (1–5).

TSP is present transiently in wound environments and its synthesis is rapidly induced by growth factors, including TGF-β (50). TSP is detectable in incisional wound margins for 2–7 days, after which it localizes around vascular channels near the wound. Although the role of TSP is not yet clearly understood, it has been speculated that TSP may facilitate cell migration into the wound site or possibly act as a localized growth promoting agent (49).

There are three sequences in TSP known as type 1 repeats. Each repeat consists of approximately 60 amino acids, has six conserved cysteine residues and has approximately 47% sequence homology to similar repeats found in the human complement component, properdin. Within the type 1 repeats of TSP, there are two well defined consensus sequences, CSVTCG (SEQ ID NO:1) and WSXW (SEQ ID NO:2). CSVTCG (SEQ ID NO:1) inhibits metastasis of melanoma cells in a murine lung colonization assay (Tuszynski et al., 1992), and promotes cell adhesion possibly by mediating interactions of TSP with sulfated glycoconjugates (53,54). The anti-angiogenic activity of TSP might be, in part, due to CSVTCG (SEQ ID NO:1). Tolsma et al. showed that CSVTCG (SEQ ID NO:1) inhibits angiogenesis in vivo using a corneal neovascularization assay (55).

The sequence WSXW (SEQ ID NO:2) binds specifically to sulfated glycoconjugates and promotes cell adhesion and chemotaxis (56). The binding of TSP to the gelatin-binding domain of fibronectin can be blocked using the peptide GGWSHW (SEQ ID NO:3), suggesting WSHW (SEQ ID NO:4) may also promote matrix protein interactions (57). This sequence is also conserved within members of the TGF-β and cytokine receptor superfamilies (58,59).

This invention provides TSP peptides which activate latent TGF-β and TSP peptides which inhibit activation of latent TGF-β.

TSP is a potential physiological regulator of TGF-β activity. These peptides from TSP can both positively and negatively modulate TGF-β levels at nanomolar to micromolar concentrations, and, therefore, can be used as therapeutic agents in vivo for the promotion of wound healing and inhibition of fibrosis.

SUMMARY OF THE INVENTION

The invention provides a method of stimulating TGF-β activity, comprising contacting latent TGF-β with an amount of an activating peptide effective to convert latent TGF-β to active TGF-β. Also provided is a method of inhibiting the stimulation of TGF-β activity, comprising contacting latent TGF-β with an amount of an inhibiting peptide effective to inhibit the conversion of latent TGF-β to active TGF-β.

The invention also provides a method of enhancing wound healing, comprising administering to the wound site an amount of an activating peptide effective to convert latent TGF-β to active TGF-β, the activation of TGF-β resulting in enhanced wound healing.

A method of preventing fibrosis stimulated by TGF-β in pathology also provided. The method comprises administering to the site of potential fibrosis an amount of inhibiting peptide effective to inhibit conversion of latent TGF-β to active TGF-β, resulting in reduced fibrosis.

The invention also provides a method of blocking TGF-β-mediated inhibition of endothelial cell proliferation comprising contacting the endothelial cells with an inhibiting peptide effective to inhibit conversion of latent TGF-β to active TGF-β, resulting in proliferation of endothelial cells.

DESCRIPTION OF THE PREFERRED EMBODIMENT

The present invention may be understood more readily by reference to the following detailed description of specific embodiments and the Examples included herein.

In one embodiment, the present invention provides a method of stimulating TGF-β activity, comprising contacting latent TGF-β with an amount of purified thrombospondin or a purified activating peptide effective to convert latent TGF-β to active TGF-β. "Activated TGF-β" or "TGF-β activity" as used herein describes the TGF-β protein present in a conformation whereby the TGF-β protein exerts an effect on cells to which it is exposed, the effect being proliferation, differentiation, angiogenesis, etc. "Latent TGF-β" as used herein means the TGF-β protein present in a conformation whereby the active domain of the TGF-β protein is complexed to LAP and therefore, does not exert an effect on cells to which it is exposed. The term "activating peptide" as used herein is defined as a peptide sequence or peptide mimetic, either synthetic, or generated from a native protein or by recombinant methods, comprising a minimum of three amino acids which, when exposed to latent TGF-β, converts latent TGF-β to activated TGF-β. The peptides of the invention correspond to sequences of TSP or they can be derived from the functional sequences of TSP. The term "purified" as used herein means separated from other proteins, peptides and contaminants.

In the method of stimulating TGF-β activity, the activating peptide can be from the first, second and third type 1 repeat regions of TSP. For example, SEQ ID NOS: 5, 9, 14, 15 and 16 are from the second type 1 repeat region. As used herein, "second type 1 repeat region" means the second type 1 repeating sequence unit, as measured from the amino terminus of the three type 1 repeats and consisting of amino acids 412–473 of human TSP1. The activating peptide can be selected from the group consisting of: KRFK (SEQ ID NO:5), HRFK (SEQ ID NO:6), RKPK (SEQ ID NO:7), QRFK (SEQ ID NO:8), KRFKQDGG (SEQ ID NO:9), RWRPWTAWSE (SEQ ID NO:10), TAYRWRLSHRPKTGIRV (SEQ ID NO:11), KRFKQDGGASHASPASS (SEQ ID NO:12), KRFKQDGGASHASP (SEQ ID NO:13), KRFKQDGGWSHWSP (SEQ ID NO:14), KRFKQDGGWSHWSPWSS (SEQ ID NO:15), KRFKQDGGWSHW (SEQ ID NO:16) and KRFKQDGGWWSP (SEQ ID NO:17) or can consist of the amino acid sequence RFK (SEQ ID NO:18). The activating peptide may contain partial or full retro-inverso modifications of the sequences or appropriate non-natural amino acids. Such sequences as well as others corresponding to or derived from TSP are determined to be activating sequences by screening for TGF-β activating function in a soft agar NRK colony formation assay and an endothelial cell proliferation assay as described in the Examples.

In another embodiment, the invention provides a method of inhibiting the stimulation of TGF-β activity comprising contacting latent TGF-β with an amount of a purified inhibiting peptide effective to inhibit the conversion of latent TGF-β to activated TGF-β. As used herein, "inhibitory peptide" means a peptide sequence comprising a minimum of four amino acids derived from the functional regions of TSP which, when exposed to latent TGF-β, inhibits the conversion of latent TGF-β to active TGF-β. The purified inhibiting peptide can have a sequence that corresponds to a sequence of four consecutive amino acids of TSP, effective to inhibit the conversion of latent TGF-β to active transforming TGF-β.

In the method of inhibiting the stimulation of TGF-β activity, the inhibiting peptide can be from the first, second and third type 1 repeat region of TSP. For example, SEQ ID NOS: 25, 26, 27 and 3 are from the second type 1 repeat. The inhibiting peptide derived from TSP can consist of the amino acid sequence GGWSHW (SEQ ID NO:3) or selected from the group consisting of: WNDWI (SEQ ID NO:19), WSSWS (SEQ ID NO:20), LSKL (SEQ ID NO:21), AAWSHW (SEQ ID NO:22), DGWSPW (SEQ ID NO:23), GGWGPW (SEQ ID NO:24), WSPWS (SEQ ID NO:25), GWSHW (SEQ ID NO:26) and WSHWS (SEQ ID NO:27). The activating peptide may contain partial or full retro-inverso modifications of the sequences or appropriate non-natural amino acids. These and other sequences derived from TSP are determined to be inhibiting sequences by screening for inhibition of TGF-β activating function in a soft agar NRK colony formation assay as described in the Examples.

TGF-β is known to regulate wound healing. Thus, the present invention also provides a method of enhancing wound healing by administering to the wound site an amount of a purified activating peptide effective to convert latent TGF-β to active TGF-β, the activation of TGF-β resulting in enhanced wound healing. The activating peptides can be those described herein. As used herein, "enhanced wound healing" is defined as a statistically significant increase in the rate of wound healing, as determined by histological analysis, tensile strength and total protein and collagen content of a wound treated with an activating peptide, as compared to a similar untreated wound or a similar wound treated with an inactive peptide control. Histological analysis includes examination for the presence of fibroblasts and capillary endothelial cells, which are early signs of wound healing. One example of this method, using the peptide KRFK (SEQ ID NO:5), is provided in the Examples.

In the method of enhancing wound healing, the activating peptide can be selected from the group consisting of: KRFK (SEQ ID NO:5), HRFK (SEQ ID NO:6), RKPK (SEQ ID NO:7), QRFK (SEQ ID NO:8), KRFKQDGG (SEQ ID NO:9), RWRPWTAWSE (SEQ ID NO:10), TAYRWRLSHRPKTGIRV (SEQ ID NO:11), KRFKQDGGASHASPASS (SEQ ID NO:12), KRFKQDGGASHASP (SEQ ID NO:13), KRFKQDGGWSHWSP (SEQ ID NO:14), KRFKQDGGWSHWSPWSS (SEQ ID NO:15), KRFKQDGGWSHW (SEQ ID NO:16) and KRFKQDGGWWSP (SEQ ID NO:17) or can consist of the amino acid sequence RFK (SEQ ID NO:18). Such sequences are determined to be activating sequences which enhance wound healing by screening for enhanced wound healing in rat models of wound healing as described in the Examples.

Because TGF-β plays a role in the development of fibrosis, the present invention also provides a method of preventing fibrosis stimulated by TGF-β in pathology by administering to the site of potential fibrosis an amount of a purified inhibiting peptide effective to inhibit conversion of latent TGF-β to active TGF-β, resulting in reduced fibrosis. The inhibiting peptides can include those described herein. As used herein, "fibrosis" means the abnormal formation of fibrous tissue (60,64). "Reduced fibrosis," as used herein, is defined as the statistically significant reduction in the level of abnormal formation of fibrous tissue as determined by histological analysis, tensile strength and total protein and collagen content in a wound treated with an inhibitory peptide as compared to the level of abnormal formation of fibrous tissue in a similar untreated wound or a similar wound treated with a peptide having no activity under conditions such that fibrosis is expected to develop. One example of this method, using the TSP peptide GGWSHW (SEQ ID NO:3), is provided in the Examples.

In the method of preventing fibrosis stimulated by TGF-β in athology, the inhibiting peptide can also be selected from the group consisting of: WNDWI (SEQ ID NO:19), WSSWS (SEQ ID NO:20), LSKL (SEQ ID O:21), AAWSHW (SEQ ID NO:22), DGWSPW (SEQ ID NO:23), GGWGPW (SEQ ID NO:24), WSPWS (SEQ ID NO:25), GWSHW (SEQ ID NO:26) and WSHWS (SEQ ID NO:27). Such sequences are determined to be inhibiting sequences which prevent fibrosis by screening for prevention of fibrosis in rat models of fibrosis formation as described in the Examples.

Active TGF-β inhibits the proliferation of endothelial and epithelial cells. Thus, in another embodiment, the present invention provides a method of blocking the TGF-β mediated inhibition of endothelial or epithelial cell proliferation, comprising contacting the cells with a purified inhibiting peptide effective to inhibit conversion of latent TGF-β to active TGF-β, resulting in proliferation of the cells. As used herein, "proliferation" means an increase in the number of cells.

In the method of blocking the TGF-β-mediated inhibition of cell proliferation, the cells can be arterial endothelial cells. Other cells that can proliferate in response to this method are capillary endothelial cells. The inhibiting peptide can be selected from the group consisting of: WNDWI (SEQ ID NO:19), WSSWS (SEQ ID NO:20), LSKL (SEQ ID NO:21), AAWSHW (SEQ ID NO:22), DGWSPW (SEQ ID NO:23), GGWGPW (SEQ ID NO:24), WSPWS (SEQ ID NO:25), GWSHW (SEQ ID NO:26) and WSHWS (SEQ ID NO:27) or can consist of the amino acid sequence GGWSHW (SEQ ID NO:3). Such sequences are determined to be inhibiting sequences by screening for TGF-β-mediated inhibition of cell proliferation, as described in the Examples.

The invention provides TGF-β activating and inhibiting peptides derived from the functional sequences of TSP. The present invention also provides a purified peptide having 3 to 30 amino acids, wherein the peptide comprises a subsequence $R_1$-$X_1$-$X_2$-$X_3$-$R_2$, wherein $X_1$ is selected from the group onsisting of Arg and Lys, $X_2$ is selected from the group consisting of Pro and he, $X_3$ is selected from the group consisting of Lys and Arg, $R_1$ is $H_2$, acyl, or a eptide from 1 to 26 amino acids, $R_2$ is H, NH2, or a peptide of from 1 to 26 mino acids, and wherein the peptide converts latent TGF-β to active TGF-β.

The purified peptide can be selected from the group consisting of: RFK (SEQ ID NO:18) KRFK (SEQ ID NO:5), HRFK (SEQ ID NO:6), RKPK (SEQ ID NO:7), QRFK (SEQ ID NO:8), KRFKQDGG (SEQ ID NO:9), TAYRWRLSHRPKTGIRV (SEQ ID NO:11), and KRFKQDGGASHASPASS (SEQ ID NO:12) or can consist of the amino acid sequence RWRPWTAWSE (SEQ ID NO:10).

The purified peptide can be conjugated to a water soluble polymer using standard protein conjugation protocols such as these described in Harlow and Lane (61). For example, suitable water soluble polymers include polysucrose, dextran, polyethylene glycol and polyvinyl alcohol.

The purified peptide can also be selected from the group consisting of partial and full retro-inverso peptide sequences. As used herein, "partial and full retro-inverso peptide sequences" means peptide sequences, determined to be either activating or inhibiting, which comprise some D-amino acids (partial) or consist entirely of D-amino acids (full), gem-diaminoalkyl residues, and alkylmalohyl residues. These can have unmodified termini, or can include appropriate alkyl, acyl, or amine substitutions to modify the charge of the terminal amino acid residues.

The present invention further provides purified peptides consisting of the amino acid sequences LSKL (SEQ ID NO:21) and acetyl-WHSWAA-NH2 (SEQ ID NO:28), and their partial and full retro-inverso peptide sequences.

Due to the relatively short half-life of peptides in vivo, the effects of modified peptides with longer half-lives can be examined. For example, the retro-inverso amino acid sequences (i.e., composed of D-amino acids) of the peptides described herein, such as the KRFKQDGGWSHWSPWSS (SEQ ID NO:15) and GGWSHW (SEQ ID NO:3) peptides, can be employed as described. These are expected to have a longer half life, because D-amino acids cannot be metabolized by cells as can naturally occurring L-forms of amino acids in proteins (65). Such retro-inverso peptides can be synthesized by standard peptide synthesis methods using commercially available D-amino acids (74). Peptide mimetics may be employed as substitutes for the natural peptide sequences based on established methods (75).

The described peptides can be applied in in vivo models to verify their modulation of TGF-β-mediated effects of wound healing and fibrosis formation. For example, rat models of wound healing can be used to evaluate the effectiveness of KRFK (SEQ ID NO:5) in stimulating wound healing in comparison to active TGF-β (62,63). An inactive peptide can be used as a negative control (e.g., TRIR (SEQ ID NO:30), KRAK (SEQ ID NO:35)). The GGWSHW (SEQ ID NO:3) peptide or other inhibiting peptides provided herein can also be examined for any effect on inhibiting wound healing by blocking TGF-β activation or for any effect in keloid formation. Inactive analogues of this peptide can be used as negative controls. The in vivo protocol of Sporn et al. (62) can be used to determine the relative effectiveness of the activating peptides described herein on wound healing. For example, 2 cm by 1 cm wire mesh wound chambers can be implanted in the backs of rats.

After a wound healing response is initiated (day 4), rats can be given daily injections of either 1000 ng TGF-β, 100–1000 nM of activating peptides, 100–1000 nM TSP, 1000 ng albumin or vehicle control per injection site at the wound site. On day 9, the animals can be sacrificed and tissues in the wound chambers can be examined histologically, assayed for total protein and collagen content (by measurement of hydroxy-proline content) and relative levels of TGF-β in the wound tissue can be examined by immunohistochemical techniques.

Alternately, a rat model of incisional wound healing as descnbed by Cromack et al. (63), can be used. In this system, a 6 cm linear incision can be made on the dorsal skin of a rat, the wound can be coapted with surgical clamps and 100–100 nM of activating peptides can be injected at the wound site in 3% methylcellulose as a vehicle. After 7–10 days, the wound strips can be harvested and evaluated for tensile strength using a tensiometer and for histological analysis as described herein.

The above-descnbed protocols can be applied to humans, because wound healing and fibrosis formation in rats, rabbits and pigs are commonly used as models for the study of wound healing and fibrosis formation in humans. (66–69).

In a clinical application, 1 μg to 100 mg of the activating peptides can be used to impregnate bandages or as part of an ointment to be applied to wound areas for the purpose of enhancing wound healing or preventing fibrosis. A skilled clinician would be able to determine, more specifically, the amount of peptides and length of treatment necessary to enhance wound healing or inhibit fibrosis.

The present peptides may be administered parenterally (e.g., intravenously), by intramuscular injection, by intraperitoneal injection, topically, transdermally, or the like, although topical administration is typically preferred. The exact amount of such compounds required will vary from subject to subject, depending on the species, age, weight and general condition of the subject, the severity of the wound or disease that is being treated, the particular compound used, its mode of administration, and the like. Thus, it is not possible to specify an exact amount. However, an appropriate amount may be determined by one of ordinary skill in the art using methods well known in the art.

For topical administration, the compounds of the present invention can be in pharmaceutical compositions in the form of solid, semi-solid or liquid dosage forms, such as, for example powders, liquids, suspension, lotions, creams, gels or the like, preferably in unit dosage form suitable for single administration of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

Parenteral administration, if used, is generally characterized by injection. Injectables can be prepared in conventional forms, either as liquid solutions or suspensions, solid forms suitable for solution or suspension in liquid prior to injection, or as emulsions. Parenteral administration can also employ the use of a slow release or sustained release system, such that a constant level of dosage is maintained (See, for example, U.S. Pat. No. 3,710,795).

Utility

The present invention also provides a bioassay for screening substances for their ability to modulate the activity of thrombospondin. For example, the present invention provides a bioassay for screening substances for their ability to enhance the activity of thrombospondin, for example, for use in therapies to promote wound healing. In another example, the present invention provides a bioassay for screening substances for their ability to inhibit the activity of TSP, for example, for use in therapies for prevention of fibrosis. Briefly, these bioassays can be performed in vitro by administering a substance to NRK cells with TSP peptides and latent TGF-β and assaying for soft agar colony formation as descnbed in the Examples. Alternatively, these bioassays can be performed in vitro by administering a substance to BAE cells and measuring cell proliferation as described in the Examples. The current use of such screening methods is set forth in the Examples, which were used to show that the peptide KRFK (SEQ ID NO:5) activates TGF-β and the peptide GGWSHW (SEQ ID NO:3) inhibits TSP-mediated activation of latent TGF-β. In vivo, these bioassays can be performed by administering substances to the wound chambers and wound sites as descnbed herein to screen for substances which play a role in wound healing and fibrosis.

The present invention further provides peptides which activate and inhibit TGF-β, which can be used as controls in in vitro bioassays for screening substances for their ability to modulate the activity of TGF-β. For example, the substances and TGF-β can be administered to NRK cells which can then be assayed for soft agar colony formation as described in the Examples. Activating or inhibiting peptides can be administered to NRK cells which can then be assayed for soft agar colony formation as positive controls for TGF-β activation and inhibition. These activating and inhibiting peptides can also be used as controls in in vivo bioassays for screening substances for their abililty to modulate the activity of TGF-β. For example, substances can be applied to the wounds and sites of potential fibrosis in the assays described in the Examples and evaluated for their ability to enhance wound healing and reduce fibrosis. The activating and inhibiting peptides can be used as controls in the described Examples.

The invention provides a method of generating a purified antibody specifically reactive with a peptide of the invention. The antibodies made can be used to detect the presence of the TSP protein. Antibodies can be made as descnbed in the art (61). Briefly, purified peptide alone or peptide conjugated to a carrier protein can be injected into an animal in an amount and in intervals sufficient to elicit an immune response. Antibodies can either be purified directly, or, for monoclonal antibodies, spleen cells can be obtained from the animal. The cells are then fused with an immortal cell line and screened for antibody secretion.

The following examples are intended to illustrate, but not limit, the invention. While they are typical of those that might be used, other procedures known to those skilled in the art may be alternatively employed.

The present invention is more particularly described in the following examples which are intended as illustrative only since numerous modifications and variations therein will be apparent to those skilled in the art.

EXAMPLES

Thrombospondin Purification

TSP was purified as previously described (34). Briefly, 8–10 units of fresh human platelets were purchased from the Birmingham American Red Cross and washed with Hepes wash buffer (10% ACD, 0.05M Hepes, 0.15M NaCl, and 5 mM dextrose), pH 7.6. The platelets were thrombin-stimulated and the platelet releasate was applied to a heparin-Sepharose™ CL-6B (Pharmacia, Piscataway, N.J.) affinity column pre-equilibrated with TBS-C (0.01M Tris-HCl, 0.15M NaCl, 0.1 mM CaCl, pH 7.4). The bound TSP was eluted with 0.55M NaCl/TBS with 1 mM CaCl and applied to an A0.5M gel filtration column (Bio-Rad, Richmond,Calif.) pre-equilibrated with TBS-C, pH 11, to remove associated TGF-β, yielding TSP stripped of TGF-β activity (sTSP). Purity was assessed by sodium dodecyl sulfate polyacrylamide gel electrophoresis (SDS-PAGE) and Coomassie blue or silver staining. No contaminating TGF-β activity was found associated with sTSP in normal rat kidney (NRK) soft agar colony formation assays.

Cells

Bovine aortic endothelial (BAE) cells were isolated from aortas obtained at a local abattoir, and were characterized by the uptake of acetylated low density lipoproteins (Dil-AcLDL) and staining for Factor VIII antigen. Cells were cultured in Dulbecco's modified Eagle's medium (DMEM; Cell-Gro, Mediatech, Herndon, Va.) supplemented with 4.5 g(L glucose, 2 mM glutamine, and 20% fetal bovine serum (FBS; Hyclone Laboratories, Logan, Utah) as previously described (33)). NRK clone 49F cells (ATCC Accession No. CRL 1570) were cultured in DMEM supplemented with 4.5 g/L glucose, 2 mM glutamine, and 10% calf serum (Hyclone Laboratories, Logan, Utah) as described (1). Calf serum was tested and chosen for low levels of active TGF-β. All cells tested negative for Mycoplasma contamination.

Peptide Synthesis

Peptides corresponding to sequences of human TSP1 as deduced from a cDNA sequence for TSP1 (70), were synthesized on a Model 9600 peptide synthesizer (Biosearch, San Rafael, Calif.) using standard Merifield solid phase synthesis protocols and t-Boc chemistry (56,57,71). Peptides were analyzed for purity by reverse-phase HPLC. Larger peptides were also characterized by amino acid sequencing.

Production of the Second Type 1 Repeat Fusion Construct

The second type 1 repeat of TSP1 corresponding to exon 9 was produced by making PCR primers which correspond to the intron-exon boundaries of exons 8–9 and 9–10. The CDNA strands were expanded by polymerase chain reaction (PCR) and expressed in *E. coli* cells using glutathione-S-transferase. The expressed proteins were characterized by sequence analysis and gel electrophoresis.

NRK Colony Formation in Soft Agar

TGF-β activity was assayed by determining colony formation of NRK cells in soft agar assays as descnbed (34), except assays were performed in 24 well tissue culture plates. Briefly, 5% Noble agar (Difco, Detroit, Mich.) was diluted ten-fold in 10% calf serum/DMEM and 0.5 ml of this 0.5% agar dilution was added per well to a 24 well tissue culture plate as a base layer and allowed to harden. A 0.2 ml sample containing 5 ng epidermal growth factor (EGF) was combined with 0.6 ml 0.5% agar and 0.2 ml ($2\times10^3$) of an NRK cell suspension in 10% calf serum/DMEM. A 0.5 ml aliquot of this 0.3% agar-sample solution was added to the cooled agar base layer and the plates were incubated for seven days at 37° C., 5% $CO_2$. Colonies greater than 62 $\mu$m in diameter (>8–10 cells) were counted. Experiments were performed in triplicate.

Activation of Latent TGF-β by sTSP or Peptides

Various concentrations of sTSP or the synthesized peptides were incubated with 2 nM (200 ng/ml) recombinant small latent TGF-β (Bristol-Myers Squibb, Seattle, Wash.) in a final volume of 0.5 ml phosphate buffered saline (PBS) for one hour at 37° C. As a positive control, 4 mM HCL was used for TGF-β activation. PBS was added to cells to establish a baseline for cell proliferation. Bovine serum albumin (BSA) (0.1%) was added to all of the samples to reduce non-specific binding of TGF-β to the tube. Samples were tested in soft agar NRK colony formation assays for TGF-β activity.

A Unique Peptide in the Second Type 1 Repeat Activates Latent TGF-β

To determine if TGF-β activation was due to either of the type 1 consensus sequences, CSVTCG (SEQ ID NO:1) and WSXW (SEQ ID NO:2), the peptides, VTCGGGVQKRSRL (SEQ ID NO:29) and KRFKQDGGWSHWSPWSS (SEQ ID NO:15), were constructed and analyzed to determine the effect of these sequences on activation of TGF-β.

Latent TGF-β was incubated with equimolar concentrations of sTSP or the above peptides and activation of TGF-β was assayed by soft agar NRK colony formation. As shown in Table I, the addition of TGFβ incubated with 11 nM sTSP increased NRK colony formation approximately twofold over the PBS baseline control. The VTCGGGVQKRSRL (SEQ ID NO:29) peptide failed to activate latent TGF-β when tested at concentrations up to 11 $\mu$M. The KRFKQDG-GWSHWSPWSS (SEQ ID NO:15) peptide increased colony formation to levels equal to those observed with sTSP. These data indicate that the mechanism by which TSP activates latent TGF-β is independent of the CSVTCG (SEQ ID NO:1) cell adhesion motif, and is associated with the KRFKQDGGWSHWSPWSS (SEQ ID NO:15) peptide.

The Amino Acid Sequence, Arginine-phenylalanine-lysine Activates Latent TGF-β

To further localize which region within the KRFKQDG-GWSHWSPWSS (SEQ ID NO:15) sequence that activates latent TGF-β, the following peptides, containing deletions at the carboxy-terminal of the peptide, were constructed: KRFKQDGGWSHWSP (SEQ ID NO:14), KRFKQDGG-WSHW (SEQ ID NO:16), KRFKQDGGWWSP (SEQ ID NO:17), KRFKQDGG (SEQ ID NO:9), KRFK (SEQ ID NO:5) and RFK (SEQ ID NO:18). Recombinant latent TGF-β was incubated with equimolar concentrations of the peptides, sTSP or the KRFKQDGGWSHWSPWSS (SEQ ID NO:15) peptide and tested for TGF-β activity. As shown in Table I, all peptides containing the amino-terminal basic residues of KRFKQDGGWSHWSPWSS (SEQ ID NO:15) activated latent TGF-β to levels comparable to sTSP. The tripeptide, RFK (SEQ ID NO:18), represented the minimal sequence required to activate TGF-β. Deletion of the WSHW (SEQ ID NO:2) sequence from the peptide failed to diminish the TGF-β activating potential, which indicates that the consensus sequence WSXW may have no direct role in the activation of latent TGF-β by TSP.

These data are consistent with the results of experiments demonstrating the inability of fusion constructs of the amino acids encoded by exon 9 to activate latent TGF-β. Exon 9 encodes amino acid residues Lys 415 through Ile 473 and contains the entire second type 1 repeat sequence of TSP1. However, the fusion protein produced lacks the KRF sequence. These data provide further support that the sequence (K)RFK is required for activation of latent TGF-β.

Certain Amino Acids Within the KRFK Sequence are Necessary for Activity

To determine which amino acids in the (K)RFK sequence are necessary for activation of latent TGF-β, peptides containing amino acid substitutions were synthesized and tested for their ability to activate latent TGF-β. The results of this experiment are shown in Table II.

As shown in Table II, the peptide, KRFK (SEQ ID NO:5), activated latent TGF-β twofold over the baseline control.

The peptide, TRIR (SEQ ID NO:30) (the corresponding sequence in the second type 1 repeat in TSP2), did not activate latent TGF-β, indicating that the activation of TGF-β is a function specific to TSP1.

The substitution of Lys 412 with amine group-containing residues, Gln (QRFK (SEQ ID NO:8)) or His (HRFK (SEQ ID NO:6)), did not diminish activity. Substitution of Lys 412 with Ala (ARFK (SEQ ID NO:31)), which lacks an amine group, abrogated activity (Table II).

Arg 413 is also important for activity. Arg can be replaced with Lys (KKFK (SEQ ID NO:32)) without diminishing activity, but substitution with a Gln, which lacks a positively charged amine group, (KQFK (SEQ ID NO:33)) abolishes activity. This suggests that a positively charged amine or guanidino group in position 413 is necessary for activity. Similarly, substitution of Lys 415 with Gln (KRFQ(SEQ ID NO:34)) results in loss of activity.

As further demonstrated in Table II, Phe 414 is required for activity. Substituting Ala (KRAK (SEQ ID NO:35)) for Phe 414 results in loss of activity. Other aromatic residues such as Tyr (KRYK (SEQ ID NO:36)) or Trp (KRWK (SEQ ID NO:37) cannot substitute for Phe 414, because these amino acid substitutions inactive the peptide. These experiments demonstrate a specific requirement for Phe in this position.

The tripeptide, RFK (SEQ ID NO: 18) activated latent TGF-β 2.5 old over baseline controls. However, substitution of Lys 415 with Arg (RFR SEQ ID NO:43)) abolished activity, as did replacement of both Phe 414 and Lys 415 with Trp and Arg (RWR (SEQ ID NO:44)), respectively (Table II).

In addition, a peptide with an inverted sequence of RFKQDGGWSHWSPWSS (SEQ ID NO:15), composed of D-amino acids and odified with an N-terminal acetyl and a C-terminal amide, was synthesized to obtain a peptide with a longer physiologic half-life. This retro-inverso peptide activated latent TGF-β at equimolar concentrations of sTSP. These data indicate that this peptide might have more sustained TGF-β modulating activity under physiologic (in vivo) conditions than the standard peptide.

The peptides listed in Table IV either activate or inhibit activation of latent TGF-β as determined by analysis using the experimental protocols described in the Examples herein.

Activation of Latent TGF-β by (K)RFK is Independent of Heparin-binding Activity

BBxB is a well known heparin-binding motif wherein B represents a basic amino acid (K,R,H) and x is any amino acid (72). The KRFKQDGGWSHWSPWSS (SEQ ID NO:15) peptide of TSP has been shown to bind heparin, but this activity is localized to the WSHW (SEQ ID NO:4) region of the peptide (56,71). To examine whether activation of latent TGF-β by TSP was associated with the BBxB motif, TSP peptide Hep II, ASLRQMKKTRGTLLA-LERKDHS (SEQ ID NO:38) (residues 74–95), which contains the BBxB motif and binds heparin (73), and a second heparin-binding TSP peptide lacking this consensus motif, Hep I, ELTGAARKGSGRRLVKGPD (amino acids 17–35) (SEQ ID NO:39), were analyzed for TGF-β activating capability. Neither Hep I nor Hep II activated latent TGF-β when assayed at concentrations up to 11 μM. These results demonstrate that activation of latent TGF-β is a specific function of the KRFK (SEQ ID NO:5) sequence of TSP and is not dependent upon the BBxB motif.

Because heparin is an anionic polysaccharide, experiments were conducted to determine if heparin blocked TGF-β activation by either sTSP or the peptides. It was found to have no effect. Based on these results, it was determined that the binding/activation of latent TGF-β by sTSP or the peptides is not mediated via carbohydrate interactions.

The RFK Sequence Present in other Proteins Does not Have TGF-β Activating Function Calcineurin (Sigma Chemicals, St. Louis, Mo.) and BSA, both of which contain the RFK (SEQ ID NO:5) sequence, were examined to determine if activation of latent TGF-β by this sequence is a function of this peptide sequence in other proteins. Latent TGF-β was incubated with equimolar amounts of sTSP, calcineurin, or BSA and assayed for activation. As determined by soft agar NRK colony formation, only sTSP activated TGF-β, indicating that the RFK (SEQ ID NO:5) sequence as it is presented within the calcineurin (KRFK (SEQ ID NO:5)) and BSA (HRFK (SEQ ID NO:6)) proteins lacks the TGF-β activity function.

Modification of the Trp Residues in the Larger Peptides Results in a Loss of Activity The above results show that the sequence (K)RFK is directly responsible for the activation of latent TGF-β by sTSP. To determine whether other residues in the larger peptides are important for TGF-β activation, amino acid residues Trp 420, Trp 423 and Trp 426 were all substituted to Ala residues in the KRFKQDGGWSHWSPWSS (SEQ ID NO:15) peptide and KRFKQDGGWSHWSP (SEQ ID NO:14) peptide to produce the peptides KRFKQDG-GASHASPASS (SEQ ID NO:12) and KRFKQDG-GASHASP (SEQ ID NO:13) and each of these were tested for TGF-β activating potential. Latent TGF-β was incubated with increasing concentrations of each of the four peptides or TSP and assayed for NRK colony forming activity. The substitution of Trp residues with Ala residues abolished the TGF-β activating function of the Trp-containing peptides at the nanomolar concentrations previously shown to be effective for the unmodified peptides or sTSP. However, peptides lacking the Trp residues activated latent TGF-β when applied at concentrations greater than 1 μM. These data show that while the (K)RFK sequence alone is sufficient to activate latent TGF-β, other amino acid specificities appear to be required to properly orient the (K)RFK sequence within larger peptides and, similarly, within intact TSP.

The Sequence GGWSHW Inhibits sTSP-mediated Activation of Latent TGF-β

To determine whether the GGWSHW (SEQ ID NO:3) sequence competitively blocks the activation of TGF-β by the TSP trimer, latent TGF-β was incubated with sTSP in the presence of increasing concentrations of the peptide GGW-SHW (SEQ ID NO:3) and assayed for activation. In a soft agar NRK colony formation assay, TGF-β, combined with only sTSP up to concentrations of 11 nM, increased colony formation by approximately twofold over PBS baseline controls. However, when latent TGF-β was incubated with 11nM sTSP in the presence of a 100-fold molar excess (1.1 μM) of the GGWSHW (SEQ ID NO:3) peptide, TGF-β activity was completely inhibited. The inhibition of sTSP-mediated activation of latent TGF-β by the GGWSHW (SEQ ID NO:3) peptide is dependent on the peptide concentration, with 100% inhibition observed after applying 1.1 μM of the peptide.

Members of the TGF-β receptor superfamily also contain the sequence WSXW (SEQ ID NO:2) and it is possible that the decrease in activity observed may be due to competition of the peptide with active TGF-β for TGF-β receptor binding sites rather than a physical blocking of TSP-TGF-β interactions. To examine this possibility, human platelet TGF-β (R&D Systems, Minneapolis, Minn.) was activated according to the manufacturer's instructions with 4 mM HCl and pre-incubated with 1.1 μM of the GGWSHW (SEQ ID NO:3) peptide for 30 minutes to maximize the possible interactions between the peptide and TGF-β. The TGF-β activity of this sample was assayed by soft agar NRK colony formation assay and compared with the TGF-β activity of activated human platelet TGF-β incubated without the peptide. The GGWSHW (SEQ ID NO:3) peptide had no effect on the activation of TGF-β as compared to human platelet TGF-β alone. Thus, the inhibitory effect of the GGWSHW (SEQ ID NO:3) peptide does not appear to be at the level of competitive blocking of TGF-β receptor binding sites.

The Sequence GGWSHW Blocks TGF-β-mediated Inhibition of Endothelial Cell Growth

BAE cells were seeded at $5 \times 10^3$ cells/well in a 24 well plate (Corning, Corning, N.Y.) and allowed to attach overnight at 37° C., 5% $CO_2$. The wells were washed once with DMEM containing no fetal bovine serum (FBS). Samples of the described peptides or intact sTSP were added in 0.5 ml 2.5% FBS/DMEM and allowed to incubate for four days at 37° C., 5% $CO_2$. Cells were fed after 48 hrs with additional sTSP or peptides and incubated an additional 48 hrs in a total volume of 1 ml of medium. Cells were then trypsinized and counted on a Coulter Cell Counter model ZM (Coulter Electronics, Hialeah, Fla.). Inhibiting peptides resulted in higher levels of cell proliferation compared to peptides having no activity.

Since one of the in vitro activities of TGF-β is to inhibit endothelial cell growth and this biological activity can be facilitated by TSP activation of latent TGF-β, then the GGWSHW (SEQ ID NO:3) peptide that blocks TSP activation of latent TGF-β should potentially block TGF-β-mediated inhibition of BAE cell growth by preventing the ability of TSP to activate latent TGF-β. In these experiments, we observed that GGWSHW (SEQ ID NO:3) in 1000–10,000-fold molar excess blocked 36–47% of TSP-mediated BAE growth inhibition. These experiments suggest that the inhibitory GGWSHW (SEQ ID NO:3) peptide can be an effective reagent to block TSP activation of latent TGF-β in a cellular environment. Other inhibiting peptides are expected to have the same effect on cell proliferation because of their similar action on TGF-β.

The Sequence KRFKQDGGWSHWSPWSSC (SEQ ID NO:45) Inhibits Proliferation of Endothelial Cells Corneal bovine endothelial cells (BCE cells) were used at passages 2 through 8 (76). BCE cell cultures were maintained in DMEM (low glucose), containing 10% FCS, 4 mM glutamine, 2.5 μg/ml amphotericin B, and 500 U/ml each of penicillin G potassium and streptomycin sulfate (all media components were from Biofluids Inc., Rockville, Md.). BCE cells were grown at 34° C. in 5% $CO_2$. The media were changed every 2–3 days.

Endothelial cell proliferation was measured using the CELL TITER 96™ assay (Promega, Madison, Wis.). $5 \times 10^3$ cells were plated into each well of a 96-well culture plate in 0.5 or 5% FCS-containing medium together with the indicated concentrations of growth effectors. After 72 h, 15 μl of dye solution was added to each well, and the plates were incubated for an additional 4 h. Solubilization solution was added, and absorbance at 570 nm was determined after 24 h as described by the manufacturer.

The activating peptide KRFKQDGGWSHWSPWSSC (SEQ ID NO:45) conjugated to FICOLL was a potent inhibitor of endothelial cell proliferation, with an inhibitory concentration 50 ($IC_{50}$) consistently less than 1 μM. The FICOLL carrier without peptide was inactive. The FICOLL conjugate of the activating peptide GGWSHWSPWSSC (SEQ ID NO:46), which lacks the amino terminal basic amino acid sequence, was also strongly active for inhibiting proliferation of endothelial cells. Similar inhibitory activities were observed using cells grown in 0.5% of 5% fetal calf serum. Other peptides that activate TGF-β should have the same effect because of their action on TGF-β.

Enhancement of Wound Healing by Administration of the KRFK Peptide

A 2 cm by 1 cm wire mesh wound chamber is implanted into the backs of rats. After a wound healing response is initiated (day 4), the rats are given daily injections of 100–1000 nM KRFK (SEQ ID NO:5), 1000 ng TGF-β, 1000 ng albumin or vehicle control per injection site at the wound site. On day 9, the animals are sacrificed and tissues in the wound chamber are examined histologically and assayed for total protein and collagen content (by measurement of hydroxy-proline content). Relative levels of TGF-β are examined in the wound tissue by immunohistochemical techniques.

Alternatively, a six cm linear incision is made in the dorsal skin of a rat, the wound is coapted with surgical clamps and 100–1000 nM KRFK, 1000 ng TGF-β, 1000 ng albumin (in 3% methylcellulose as a vehicle) or vehicle control per injection site is injected at the wound site. Other controls could include inactive analogs of KRFK (SEQ ID NO:5), such as KRAK (SEQ ID NO:35), TRIR (SEQ ID NO:30) or KRWK (SEQ ID NO:37). After 7–10 days, wound strips are harvested and evaluated for tensile strength using a tensiometer and for histological analysis as described above. Enhanced wound healing would be determined by histological evaluation of cellularity of the wound site (measurement of DNA content), the presence of collagen fibrils, and of re-epithelialization of the wound surface. Clinicians familiar with this condition would be able to make a determination that a statistically significant increase in the rate of wound healing has occurred. For example, one skilled in the art could evaluate how much change in the DNA content is indicative of enhanced wound healing in a treated wound relative to an untreated wound. Also, a skilled artisan could readily determine the amount of re-epithelialization required for enhanced wound healing. Furthermore, one skilled in the art could readily assess the tensile strength of a wound in evaluating enhanced wound healing.

Prevention of Fibrosis by Administration of the GGWSHW Peptide

A 2 cm by 1 cm wire mesh wound chamber is implanted into the backs of rats. After a wound healing response is initiated (day 4), the rats are given daily injections of 100–1000 nM GGWSHW (SEQ ID NO:3) peptides, 100–2000 ng TGF-β, 100–2000 ng albumin or vehicle control per injection site at the wound site. On day 9, the animals are sacrificed and tissues in the wound chamber are examined histologically and assayed for total protein and collagen content (by measurement of hydroxy-proline content). Relative levels of TGF-β are examined in the wound tissue by immunohistochemical techniques.

Alternatively, a six cm linear incision is made in the dorsal skin of a rat, the wound is coapted with surgical clamps and 100–1000 nM GGWSHW (SEQ ID NO:3), 100–2000 ng TGF-β, 100–2000 ng albumin (in 3% methylcellulose as a vehicle) or vehicle control per injection site is injected into the wound site. Other controls could include inactive analogs of GGWSHW (SEQ ID NO:3), such as SHWWSS (SEQ ID NO:40), GGWSHY (SEQ ID NO:41) and GGWSKW (SEQ ID NO:42). After 7–10 days, the wound strips are harvested and evaluated for tensile strength using a tensiometer and for histological analysis as described above. The primary measure of fibrosis would be an evaluation of the collagen content of the wound by histological analysis with a trichrome stain for connective tissue and by measurement of hydroxyproline content of a defined wound area from a punch biopsy. Clinicians familiar with this condition would be able to make a determination that a statistically significant reduction in fibrosis has occurred. For example, one skilled in the art could evaluate how much change in the collagen content of a treated wound is indicative of reduced fibrosis relative to an untreated wound. Also, a skilled artisan could readily determine the amount of hydroxyproline which is indicative of reduced fibrosis.

Topical Treatment of a Wound with TSP Peptides to Enhance Wound Healing

In a clinical application, 1 µg to 100 mg of purified activating peptides of TSP are impregnated in a bandage which is applied directly to a wound or are incorporated into an ointment which is applied directly to the wound. A skilled clinician would be able to determine the amount of peptides and length of treatment with the peptides necessary to enhance wound healing, depending on the patient's age, size and the site and condition of the wound.

Topical Treatment of a Site of Potential Fibrosis with TSP Peptides to Reduce Fibrosis In a clinical application, 1 µg to 100 mg of purified inhibiting peptides of TSP are impregnated in a bandage which is applied directly to the site of potential fibrosis or are incorporated into an ointment which is applied directly to the site of potential fibrosis. A skilled clinician would be able to determine the amount of peptides and length of treatment with the peptides necessary to reduce fibrosis, depending on the patient's age, size and the condition of the site of potential fibrosis.

TABLE I

The minimal sequence required for activation of latent TGF-β is the RFK peptide sequence of TSP.

| Sequence | Fold Activation of Latent TGF-β over Baseline |
| --- | --- |
| sTSP | 2x ± 0 |
| VTCGGGVQKRSRL (SEQ ID NO:29) | none |
| KRFKQDGGWSHWSPWSS (SEQ ID NO:15) | 2x ± 10 |
| KRFKQDGGWSHWSP (SEQ ID NO:14) | 2.3x ± 0.2 |
| KRFKQDGGWSHW (SEQ ID NO:16) | 1.9x ± 0.2 |
| KRFKQDGGWWSP (SEQ ID NO:17) | 2.1x ± 0.2 |
| KRFKQDGG (SEQ ID NO:9) | 2.1x ± 0.1 |
| KRFK (SEQ ID NO:5) | 2x ± 0.1 |
| RFK (SEQ ID NO:18) | 2.5x ± 0.5 |

TABLE II

Certain amino acids within the KRFK sequence of TSP are necessary for TGF-β stimulating activity.

| Sequence | Fold Activation of Latent TGF-β over Baseline |
| --- | --- |
| sTSP | 2x ± 0 |
| KRFK (SEQ ID NO:5) | 2x ± 0.1 |
| TRIR (SEQ ID NO:30) | none |
| QRFK (SEQ ID NO:8) | 2X ± 0 |
| HRFK (SEQ ID NO:6) | 2X ± 0 |
| KKFK (SEQ ID NO:32) | 2.2 ± 0.15 |

TABLE II-continued

Certain amino acids within the KRFK sequence of TSP are necessary for TGF-β stimulating activity.

| Sequence | Fold Activation of Latent TGF-β over Baseline |
| --- | --- |
| KQFK (SEQ ID NO:33) | none |
| KRFQ (SEQ ID NO:34) | none |
| KRAK (SEQ ID NO:35) | none |
| KRYK (SEQ ID NO:36) | none |
| KRWK (SEQ ID NO:37) | none |
| RFK (SEQ ID NO:18) | 2.5x ± 0.5 |
| RFR (SEQ ID NO:43) | none |
| RWR (SEQ ID NO:44) | none |

TABLE III

The inhibitory peptide, GGWSHW, blocks TGF-β-mediated inhibition of BAE cell growth.

| Treatment of BAE Cells | Cells/Well on Day 4 |
| --- | --- |
| 2.5% FBS | 165,491 ± 1530 |
| TSP 1.0 µg/ml | 64,331 ± 3841 |
| TSP + GGWSHW (SEQ ID NO: 3) (1.1 µM) | 100,522 ± 2990 |
| TSP + GGWSHW (SEQ ID NO:3) (11 µM) | 112,276 ± 3730 |

TABLE IV

Peptides which Activate or Inhibit Activation of Latent TGF-β

| Activating Peptides | Inhibiting Peptides |
| --- | --- |
| KRFK (SEQ ID NO:5) | WNDWI (SEQ ID NO:19) |
| HRFK (SEQ ID NO:6) | GGWSHW (SEQ ID NO:3) |
| RKPK (SEQ ID NO:7) | LSKL (SEQ ID NO:21) |
| QRFK (SEQ ID NO:8) | DGWSPW (SEQ ID NO:23) |
| RFK (SEQ ID NO:18) | GGWGPW (SEQ ID NO:24) |
| KRFKQDGG (SEQ ID NO:9) | WSPWS (SEQ ID NO:25) |
| RWRPWTAWSE (SEQ ID NO:10) | GWSHW (SEQ ID NO:26) |
| TAYRWRLSHRPKTGIRV (SEQ ID NO:11) | WSHWS (SEQ ID NO:27) |
| KRFKQDGGASHASPASS (SEQ ID NO:12) | WSSWS (SEQ ID NO:20) |
| KRFKQDGGASHASP (SEQ ID NO:13) | retro-inverso acetyl WHSWAA (SEQ ID NO:28)-NH2 |
| KRFKQDGGWSHWSPWSSC (SEQ ID NO:45) | AAWSHW (SEQ ID NO:22) |
| GGWSHW2SPWSSC (SEQ ID NO:46) | |

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES

1. Allen-Hoffman, B. L., C. L. Crankshaw, and D. F. Mosher. 1988. Transforming Growth Factor β Increases Cell Surface Binding and Assembly of Exogenous (Plasma) Fibronectin by Normal Human Fibroblasts. *Mol. Cell Biol.* 8:4234–4242.

2. Bagavandoss, P., and J. W. Wilks. 1990. Specific Inhibition of Endothelial Cell Proliferation by Thrombospondin. *Biochem. Biophys. Res. Commun* 170:867–872.
3. Barnard, J. A, R. M. Lyons, and H. L. Moses. 1990. The Cell Biology of TGF-β. *Biochem. Biophys. Res. Commun.* 163: 56–63.
4. Bodmer, S., K Strommer, K. Frei, C. Siepl, N. de Tribolet, I. Heid, and A. Fontana. 1989. Immunosuppresion and Transforming Growth Factor-β in Glioblastoma. Preferential Production of Transforming Growth Factor-β$_2$. *J. Immunol.* 143:3222–3229.
5. Bornstein, P. 1992. Thrombospondins—Structure and egulation of Expression. *FASEB Jounal.* 6:3290–3299.
6. Brown, P. D., L. M. Wakefield, A. D. Levinson, and M. B. Sporn. 1990. Physiochemical Activation of Recombinant Latent Transforming Growth Factor-betas 1,2, and 3. *Growth Factors* 3:35–43.
7. Browne, P. C., J. J. Miller, and T. C. Detwiler. 1988. Kinetics of the Formation of Thrombin-Thrombospondin Complexes: Involvement of a 77-kDa Intermediate. *Arch. Biochenl. and Biophys.* 151:534–538.
8. Brunner, A. M., L. E. Gentry, J. A. Cooper, A. F. Purchio. 1988. Recombinant Type I Transforming Growth Factor β Precursor Produced in Chinese Hamster Ovary Cells is Glycosylated and Phosphorylated. *Mol. Cell Biol.* 8:2229–2232.
9. Brunner, A. M., H. Marquardt, A. R. Malacko, M. N. Lioubin, and A. F. Pur chio. 1989. Site-Directed Mutagenesis of Cysteine Residues in the Pro Region of the Transforming Growth Factor β1 Precursor. *J. Biol. Chem.* 264:13660–13664.
10. Cheifetz, S. and J. Massague. 1989: Transforming Growth Factor-β (TGF-β) Receptor Proteoglycan. *J. Biol. Chem.* 264:12025–12028.
11. Dardik, R. and J. Lahav. 1991. Cell-binding domain of endothelial cell thrombospondin: localization to the 70-kDa core fragment and determination of binding characteristics. *Biochemistry* 30:9378–9386.
12. Dennis, P. A., D. B. Rifkin. 1991. Cellular Activation of Latent Transforming Growth Factor-β Requires Binding to the Cation-Independent Mannose-6-Phosphate/Insulin-like Growth Factor Type II Receptor. *Proc. Nat. Acad. Sci. USA.*
13. Flaumenhaft, R., M. Ave, P. Mignatti, and D. B. Rifkin. 1992. bFGF Induced Activation of Latent TGF-β in Endothelial Cells: Regulation of Plasminogen Activator Activity. *J. Cell. Biol.* 118:901–909.
14. Frazier, W. A. 1987. Thrombospondin: a Modular Adhesive Glycoprotein of Platelets and Nucleated Cells. *J. Cell. Biol.* 105:625–632.
15. Gentry, L. E., M. N. Lioubin, A. F. Purchio, and H. Marquardt. 1988. Molecular Events in the Processing of Recombinant Type 1 Pre-Pro-Transforming Growth Factor beta to the Mature Polypeptide. *Mol. Cell. Biol.* 8:4162–4168.
16. Gentry, L. E., N. R. Webb, J. Lim, A. M. Brunner, J. E. Ranchalis, D. R. Twardzik, M. N. Lioubin, H. Marquardt, A. F. Purchio. 1987. Type I Transforming Growth Factor Beta: Amplified Expression and Secretion of Mature and Precursor Polypeptides in Chinese Hamster Ovary Cells. *Mol. Cell Biol.* 7:3418–3427.
17. Gentry, L. E. and B. W. Nash. 1990. The Pro Domain of Pre-Pro Transforming Growth Factor-β1 when Independently Expressed is a Functional Binding Protein for the Mature Growth Factor. *Biochem.* 29:6851–6857.
18. Hannan, R. L., Kourembanas, K. C. Flanders, S. J. Rogelj, A. B. Roberts, D. V. Faller, and M. Klagsbrun. 1988. Endothelial cells synthesize basic fibroblast growth factor and transforming growth factor beta. *Growth Factors* 1:7–17.
19. Huber, D., A. Fontant, and S. Bodmer. 1991. Activation of Human Platelet Derived Latent Transforming Growth Factor-β 1 by Human Glioblastoma *Cells. Biochem. J.* 277:165–173.
20. Jullien, P., T. M. Berg, D. A. Laurence. 1989. Acidic Cellular Environments: Activation of Latent TGF-β and Sensitization of Cellular Responses to TGF-β and EGF. *Int. J. Cancer.* 43:886–891.
21. Kovacina, K. S., G. Steele-Perkins, A. F. Purchio, M. Lioubin, K. Miyazono, C-H. Heldin, and R. A. Roth. 1989. Interactions of Recombinant and Platelet Transforming Growth Factor-β 1 with the Insulin-like Growth Factor II/Mannose 6-Phosphate Receptor. *Biochem Biophys. Res. Commun.* 160:393403.
22. Lyons, R. M., J. Keski-Oja, and H. L. Moses. 1988. Proteolytic Activation of Latent Transforming Growth Factor-β from Fibroblast Conditioned Medium. *J. Cell Biol.* 106:1659–1665.
23. Lyons, R. M., L. E. Gentry, A. F. Purchio, and H. L. Moses. 1990. Mechanism of Activation of Latent Recombinant Transforming Growth Factor β1 by Plasmin. *J. Cell Biol.* 110:1361–1367.
24. Majack, R. A., S. Coates-Cook, and P. Bornstein. 1986. Control of Smooth Muscle Cell Growth by Components of the Extracellular Matrix: Autocrine Role for Thrombospondin. *Proc. Nat. Acad. Sci. USA* 83:9050–9054.
25. Massague J., T. Endo, B. Nadal-Ginard, and S. Cheifetz. 1986. Type β Transforming Growth Factor is an Inhibitor of Myogenic Differentiation. *Proc. Nat. Acad. Sci. USA* 83:8206–8210.
26. Massague, J. et al. 1992. Transforming Growth Factor-β. Cancer Surveys 12: Tumour Suppressor Genes, the Cell Cycle and Cancer.
27. Miyazono, K. U. Hellman, C. Wernstedt, and C. H. Heldin. 1988. Latent High Molecular Weight Complex of Transforming Growth Factor β1; Purification from Human Platelets and Structural Characterization. *J. Biol. Chem.* 263:6407–6415.
28. Miyazono, K. C. H. Heldin. 1989. Role for Carbohydrate Structures in TGF-β Latency. *Nature* (London) 338:158–160.
29. Mooradian, D. L., R. C. Lucas, J. A. Weatherbee, and L. T. Furcht. 1989. Transforming Growth Factor-beta 1 Binds to Immobilized Fibronectin. *J. Cell. Biochem.* 41:189–200.
30. Mosher, D. F. 1990. Physiology of Thrombospondin. *Annu. Rev. Med.* 41:85–97.
31. Mueller, G., J. Behrens, U. Nussbaumer, P. Bohlen, and W. Birchmeier. 1987. Inhibitory Action of TGF-β on Endothelial Cells. *Proc. Nat. Acad. Sci. USA.* 84:5600–5604.
32. Murphy-Ullrich, J. E., L. G. Westrick, J. D. Esko, and D. F. Mosher. 1988. Altered metabolism of thrombospondin by Chines Hamster Ovary cells defective in glycosaminoglycan synthesis. *J. Biol. Chem.* 263:6400–6406.
33. Murphy-Ullrich, J. E., and M. Hk. 1989. Thrombospondin Modulates Focal Adhesions in Endothelial Cells. *J. Cell Biol.* 109:1309–1319.
34. Murphy-Ullrich, J. E., S. Schultz-Cherry, and M. Hook. 1992. Transforming Growth Factor-β Complexes With Thrombospondin. *Mol Biol. of the Cell* 3:181–188.
35. Paralkar, V. M., S. Vukicevic, and A. H. Reddi. 1991. Transforming Growth Factor Beta Type I Binds to Collagen IV of Basement Membrane Matrix:Implications for Development. *Developmental Biol.* 143:303–308.

36. Phan, S. H., R. G. Dillon, B. M. McGarry, and V. M. Dixit. 1989. Stimulation of Fibroblast Proliferation by Thrombospondin. *Biochem. Biophys. Res. Commun.* 163:56–63.
37. Pircher, R., P. Jullien and D. A. Lawrence. 1986. β-Transforming Growth Factor is Stored in Human Blood Platelets as a Latent High Molecular Weight Complex. *Biochem. Biophys. Res. Comm.* 136:30–37.
38. Purchio, A. F., J. A. Cooper, A. M. Brunner, M. N. Lioubin, L. E. Gentry, K. S. Kovacina, R. A. Roth, H. Marquardt. 1988. Identification of Mannose-6-Phosphate intwo Asparagine-Linked Sugar Chains of Recombinant Transforming Growth Factor β1 Precursor. *J. Biol Chem.* 264:14211–14215.
39. Roberts, A. B., M. B. Sporn, R. K. Assoian, J. M. Smith, N. S. Roche, L. M. Wakefield, U. I. Heine, L. A. Liotta, V. Falanga, J. H. Kehrl, A. S. Fauci. 1986. Transforming growth Factor Type-beta: Rapid Induction of Fibrosis and Angiogenesis in vivo and Stimulation of Collagen Formation in vitro. *Proc. Nat. Acad. Sci.* 83:4167–4171.
40. Sato, Y., D. B. Rifkin. 1989. Inhibition of Endothelial Cell Movement by Pericytes and Smooth Muscle Cells: Activation of a Latent TGF-β 1-like Molecule by Plasmin During Co-Culture. *J. Cell Biol.* 109:309–315.
41. Sato, Y., R. Tsuboi, R. Lyons, H. Moses, and D. B. Rifkin. 1990. Characterization of the Activation of Latent TGF-β by Co-Cultures of Endothelial Cells and Pericytes of Smooth Muscle Cells: A Self-Regulating System. *J. Cell Biol.* 111:757–764.
42. Taraboletti, G., D. Roberts, L. A. Liotta, and R. Giavazzia. 1990. Platelet Thrombospondin Modulates Endothelial Cell Adhesion, Motility, and Growth: A Potential Angiogenesis Regulatory Factor. *J. Cell Biol.* 111:765–772.
43. Wakefield, L. M., T. S. Winokur, R. S. Hollands, K. Christopherson, A. D. Levison, and M. B. Sporn. 1990. Recombinant Latent Transforming Growth Factor Beta 1 has a Longer Plasma Half-Life in rats than Active Transforming Growth Factor beta 1, and a Different Tissue Distribution. *J. Clin. Invest.* 86:1976–1984.
44. Yamaguchi, Y., D. M. Mann, and E. Ruoslahti. 1990. Negative Regulation of Transforming Growth Factor-beta by the Proteoglycan Decorin. *Nature* 346:281–284.
45. Zentalla, A. and J. Massague. 1992. TGF-β Induces Myoblast Differentiation in the Presence of Mitogens. *Proc. Nat. Acad. Sci.* 89:5176–5180.
46. Raghow, *Chest* (Supplement, 33rd Annual Thomas L. Petty Aspen Lung Conference) 99:61S–65S (1991).
47. Mosher, 1990.
48. Frazier, 1991.
49. Lahav, *Biochimica et Biophysica Acta* 1182:1–14 (1993)
50. Penttinen et al., *PNAS*, 85:1105–1108 (1988)
51. Vogel et al., 1993.
52. Majack et al., 1988.
53. Prater et al., 1992.
54. Asch et al. 1992.
55. Tolsma et al. 1993.
56. Guo et al., *J. Biol. Chem.*, 267:19349–19355 (1992).
57. Sipes et al., *J. Cell Biol.*, 121:469477 (1993).
58. Wharton et al. 1991.
59. Bazan 1990.
60. Sandritter et al., "Color Atlas and Textbook of Histopathology," Year Book Medical Publishers, Inc., Chicago, Ill. (1979).
61. Harlow and Lane, *Antibodies, A Laboratory Manual*, Cold Springs Harbor Laboratory, Cold Spring Harbor, New York, N.Y. (1988)
62. Sporn et al., *Science*, 219:1329–1330 (1983).
63. Cromack et al., *Surgery*, 113:3642 (1993)
64. Cotron et al., "Robbins Pathologic Basis of Disease," 4th Edition, W. B. Saunder Co., Philadelphia (1989).
65. Lehninger et al., "Principles of Biochemistry," 2d Ed., (1993) Worth Publishers, New York, N.Y.
66. Amento et al, TGF-β and Wound Healing (pp. 115–123) Ciba Foundation Symposium, 57: "Clinical Applications of TGF-β," John Wiley and Sons (1991).
67. Ksander, GA et al., "Transforming Growth Factors-β1 and β2 Enhance Connective Tissue Formation in Animal Models of Dermal Wound Healing by Secondary Intent," *Annals of NY Acad Sci.*, 593:135–147 (1990).
68. Davidson, JM et al., "Manipulation of the Wound Healing Process with Basic FGF," *Annals NY Acad. Sci.*, 638:306–315 (1990).
69. Mazue, G. et al., "Preclinical and Clinical Studies with Recombinant Human Fibroblast Growth Factor," *Annals NY Acad Sci.*, 638:329–340 (1990).
70. Lawler & Hynes, *J. Cell Biol.*, 103:1635–1648 (1986).
71. Guo et al., *P.N.A.S.*, 89:2040–2044 (1992).
72. Cardin & Weintraub, *Arteriosckrosis*, 9:21–32 (1989).
73. Murphy-Ullrich et al., *J. Biol. Chem.*, 268:26784–26789 (1993).
74. Choreo and Goodman *Acc. Chem. Res.* 26:266–273 (1993).
75. Olson et al. *J. Med. Chem.* 36:3039–3049 (1993).
76. Munjal et al. (1990).

What is claimed is:

1. A peptide selected from the group consisting of RFK (SEQ ID NO: 18) KRFK (SEQ ID NO:5), HRFK (SEQ ID NO: 6), RKPK (SEQ ID NO: 7), QRFK (SEQ ID NO:8), KRFKQDGG (SEQ ID NO:9), TAYRWRLSHRPKTGIRV (SEQ ID NO:11) and KRFKQDGGASHASPASS (SEQ ID NO:12), or partial and full retro-inverso peptide sequences thereof, wherein the peptide converts latent transforming growth factor-beta to active transforming growth factor-beta.

2. The peptide of claim 1, wherein the peptide is RFK (SEQ ID NO: 18).

3. The peptide of claim 1, wherein the peptide is KRFK (SEQ ID NO: 5).

4. The peptide of claim 1, wherein the peptide is HRFK (SEQ ID NO: 6).

5. The peptide of claim 1, wherein the peptide is RKPK (SEQ ID NO: 7).

6. The peptide of claim 1, wherein the peptide is QRPK (SEQ ID NO: 8).

7. The peptide of claim 1, wherein the peptide is KRFKQDGG (SEQ ID NO: 9).

8. The peptide of claim 1, wherein the peptide is TAYRWRLSHRPKTGIRV (SEQ ID NO:11).

9. The peptide of claim 1, wherein the peptide is KRFKQDGGASHASPASS (SEQ ID NO: 12).

10. The peptide according to claim 1, wherein the peptide is selected from the group consisting of partial retro-inverso and full retro-inverso peptide sequences.

11. A peptide conjugated to a water soluble polymer wherein the peptide is selected from the group consisting of RFK (SEQ ID NO: 18) KRFK (SEQ ID NO:5), HRFK (SEQ ID NO: 6), RKPK (SEQ ID NO: 7), QRFK (SEQ ID NO:8), KRFKQDGG (SEQ ID NO:9), TAYRWRLSHRPKTGIRV (SEQ ID NO:11) and KRFKQDGGASHASPASS (SEQ ID NO: 12), or partial and full retro-inverso peptide sequences thereof.

12. A purified peptide selected from the group consisting of acetyl-WHSWAA-NH2 (SEQ ID NO:28) and LSKL (SEQ ID NO:21).

13. The peptide of claim 12, wherein the peptide is acetyl-WHSWAA-NH2 (SEQ ID NO: 28).

14. The peptide of claim 12, wherein the peptide is LSKL (SEQ ID NO: 21).

15. A peptide selected from the group consisting of the partial retro-inverso peptide sequence acetyl-WHSWAA-NH2 (SEQ ID NO:28), the full retro-inverso peptide sequence acetyl-WHSWAA-NH2 (SEQ ID NO:28), the partial retro-inverso sequence of LSKL (SEQ ID NO:21), and the full retro-inverso peptide sequence of LSKL (SEQ ID NO:21).

16. The peptide consisting of the amino acid sequence RWRPWTAWSE, defined in the Sequence Listing as SEQ ID NO:10 or partial and full retro-inverso peptide sequences thereof.

17. The peptide according to claim 16, wherein the peptide is selected from the group consisting of partial retro-inverso and full retro-inverso peptide sequences.

18. A peptide consisting of the amino acid sequence RWRPWTAWSE (SEQ ID NO:10) conjugated to a water soluble polymer.

* * * * *

UNITED STATES PATENT AND TRADEMARK OFFICE
CERTIFICATE OF CORRECTION

PATENT NO. : 6,384,189 B1
DATED : May 7, 2002
INVENTOR(S) : Murphy-Ullrich et al.

It is certified that error appears in the above-identified patent and that said Letters Patent is hereby corrected as shown below:

<u>Title page,</u>
Item [73], Assignee, should read as follows:

-- The Government of the United States as represented by the Secretary, Department of Health and Human Services, Washington, DC; UAB Research Foundation, Inc., Birmingham, AL --.

Signed and Sealed this

Twenty-fifth Day of March, 2003

JAMES E. ROGAN
*Director of the United States Patent and Trademark Office*